United States Patent [19]

Simon et al.

[11] Patent Number: 4,801,596
[45] Date of Patent: Jan. 31, 1989

[54] NITROXY AMINO PROPANOLS FOR TREATING HEART AND CIRCULATORY DISEASES

[75] Inventors: Herbert Simon, Lampertheim; Helmut Michel; Walter-Gunar Friebe, both of Mannheim; Wolfgang Bartsch, Viernheim, all of Fed. Rep. of Germany

[73] Assignee: Boehringer Mannheim GmbH, Mannheim, Fed. Rep. of Germany

[21] Appl. No.: 803,497

[22] Filed: Dec. 2, 1985

[30] Foreign Application Priority Data

Dec. 1, 1984 [DE] Fed. Rep. of Germany ....... 3443998

[51] Int. Cl.⁴ ...................... A01K 31/21; C07F 79/10
[52] U.S. Cl. ..................... 514/327; 514/509; 514/524; 546/220; 558/414; 558/482; 558/484
[58] Field of Search .................. 558/414, 482, 481; 546/226, 220; 514/255, 524, 509, 327

[56] References Cited

U.S. PATENT DOCUMENTS 4,438,143 3/1984 Koppe et al. ............... 558/416

FOREIGN PATENT DOCUMENTS 34461 8/1981 European Pat. Off. ........... 558/482

*Primary Examiner*—Anton H. Sutto
*Attorney, Agent, or Firm*—Felfe & Lynch

[57] ABSTRACT

The present invention provides new aminopropanol derivatives of the general formula:

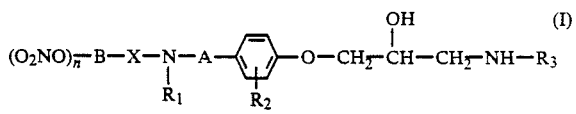

wherein A is a direct bond, a straight-chained or branched alkylene chain containing up to 3 carbon atoms or a —CO—CH$_2$— group; X is a direct bond or a carbonyl group; B is a straight-chained or branched, saturated or unsaturated alkylene chain containing up to 12 carbon atoms, in which one or two —CH$_2$— groups can also be replaced by a saturated or unsaturated alkylene ring containing 3 to 7 carbon atoms and/or by an oxygen or sulphur atom or an —S(=O)— or —S(=O)$_2$— group, n is 1, 2 or 3; R$_1$ is a hydrogen atom or a straight-chained or branched, saturated or unsaturated alkyl radical containing up to 6 carbon atoms or a —B—(ONO$_2$)$_n$ group, in which B and n have the same meanings as above, or when A is a —CO—CH$_2$— group and X is a direct bond, R$_1$ together with the nitrogen atom and a carbon atom of chain B can represent a heteroaliphatic ring containing 2 to 7 carbon atoms; R$_2$ is a hydrogen or halogen atom or a cyano, hydroxyl, amino, nitro, carboxyl, carbamoyl, ureido or sulphamoyl group or an alkyl, alkoxy, alkylamino, alkylthio, hydroxyalkyl, aminoalkyl, alkoxycarbonyl, alkylcarbonyl, alkylaminocarbonyl, alkylcarbonylamino, alkoxycarbonylamino or alkylaminocarbonylamino radical; and R$_3$ is an alkyl or nitroxyalkyl radical containing 3 to 8 carbon atoms; and the physiologically acceptable salts thereof.

The present invention also provides processes for the preparation of these aminopropanol derivatives and pharmaceutical compositions containing them, as well as intermediates for the preparation of the new aminopropanol derivatives.

11 Claims, No Drawings

NITROXY AMINO PROPANOLS FOR TREATING HEART AND CIRCULATORY DISEASES

The present invention is concerned with new aminopropanol derivatives, processes for the preparation thereof and pharmaceutical compositions containing them, as well as new intermediates for the preparation of the new aminopropanol derivatives.

Thus, according to the present invention, there are provided new aminopropanol derivatives of the general formula:

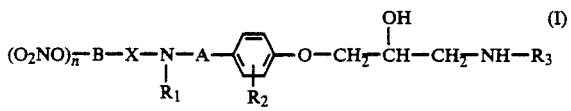

wherein A is a direct bond, a straight-chained or branched alkylene chain containing up to 3 carbon atoms or a —CO—CH$_2$— group; X is a direct bond or a carbonyl group; B is a straight-chained or branched, saturated or unsaturated alkylene chain containing up to 12 carbon atoms, wherein one or two —CH$_2$— groups can also be replaced by a saturated or unsaturated alkylene ring containing 3 to 7 carbon atoms and/or by an oxygen atom or a sulphur atom or an —S(=O)— or —S(=O)$_2$— group; n is 1, 2 or 3; R$_1$ is a hydrogen atom or a straight-chained or branched, saturated or unsaturated alkyl radical containing up to 6 carbon atoms or a —B—(ONO$_2$)$_n$ group, in which B and n have the same meanings as above, or, when A signifies a —CO—CH$_2$— group and X is a direct bond, R$_1$ together with the nitrogen atom and a carbon atom of chain B can represent a heteroaliphatic ring containing 2 to 7 carbon atoms; R$_2$ is a hydrogen or halogen atom, a cyano, hydroxyl, amino, nitro, carboxyl, carbamoyl, ureido or sulphamoyl group or an alkyl, alkoxy, alkylamino, alkylthio, hydroxyalkyl, aminoalkyl, alkoxycarbonyl, alkylcarbonyl, alkylaminocarbonyl, alkylcarbonylamino, alkoxycarbonylamino or alkylaminocarbonylamino radical; and R$_3$ is an alkyl or nitroxyalkyl radical containing 3 to 8 carbon atoms; as well as the physiologically compatible salts thereof.

The alkylene chains in the definition of A can be, for example, a methylene, ethylene, trimethylene, 1-methylethylene, 2-methylethylene or 1,1-dimethylmethylene radical, the ethylene radical being preferred.

The alkylene chain in the definition of B can be, for example, a straight-chained or branched alkylene radical containing up to 12 and preferably 2 to 6 carbon atoms, the ethylene, trimethylene, tetramethylene, pentamethylene, hexamethylene, 1-methyltrimethylene, 1,1-dimethyltrimethylene and 2,2-dimethyltrimethylene radicals being especially preferred. When a —CH$_2$— group is replaced by a cycloalkylene ring, B can be, for example, a cyclopropylene, cyclopropylenemethylene, cyclopentylene, cyclopentylmethylene, cyclohexylene, cyclohexenylene, cyclohexylenemethylene or methylenecyclohexylenemethylene radical.

The alkyl radical in the definition of R$_1$ is especially a methyl, ethyl, propyl or butyl radical. A branched alkyl radical can be, for example, an isopropyl or tert.-butyl radical and an unsaturated alkyl radical can be, for example, an allyl or methylallyl radical. When A signifies a —CO—CH$_2$— group and X is a direct bond, R$_1$ together with the nitrogen atom and a carbon atom of chain B can form a heteroaliphatic ring, for example an aziridine, pyrrolidine or piperidine ring, possibly substituted once or several times by nitroxy, nitroxyalkylene and preferably nitroxymethylene. The piperidinyl and the methylenepiperidinyl radicals are especially preferred.

The alkyl radical in the definition of R$_2$ is a straight-chained or branched, saturated or unsaturated radical containing up to 12 and preferably up to 4 carbon atoms, the methyl, ethyl, propyl, isopropyl, butyl, tert.-butyl, allyl and methylallyl radicals being especially preferred.

By an alkyl radical in the definition of R$_3$ there is to be understood a straight-chained or branched, saturated or unsaturated alkyl radical containing 3 to 8 and preferably 3 to 5 carbon atoms, the isopropyl, tert.-butyl and 2-methyl-3-butyn-2-yl radicals being especially preferred. In the case of nitroxyalkyl radicals, a hydrogen atom of the corresponding alkyl radical is replaced by a nitroxy group, the 1-nitroxy-but-3-yl radical being especially preferred.

As a rule, the compounds of general formula (I) according to the present invention contain one or two nitroxy groups, the mononitroxy compounds being preferred.

Compounds of a similar type have already been described, for example, in Federal Republic of Germany patent specifications Nos. 16 67 883; 17 93 511; 20 07 751; 21 06 209; 21 06 816; 22 53 776 and 25 03 222; in Austrian patent specification No. 334 385 and in South African patent specification Nos. 68/03130 and 68/08345.

However, the compounds there described differ from the compounds of general formula (I) according to the present invention in that they do not have an —O—NO$_2$ group. The compounds of general formula (I) according to the present invention possess valuable properties. Thus, they possess not only a β-receptor blocking activity but they also bring about a reduction of the oxygen requirement of the heart, an increase of the blood flow and a lowering of the blood pressure. Therefore, they can be used for the prophylaxis and/or treatment of heart and circulatory diseases, for example high blood pressure and angina pectoris.

The compounds of general formula (I) according to the present invention can be prepared in known manner in that (a) a compound of the general formula:

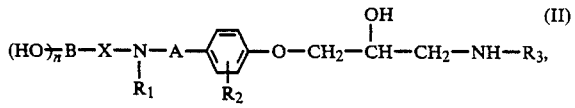

in which A, B, X, R$_1$, R$_2$, R$_3$ and n have the above-given meanings and R$_1$ can additionally be a —B—(OH)$_n$ group, is subjected to a nitrate ester formation reaction; or (b) a compound of the general formula:

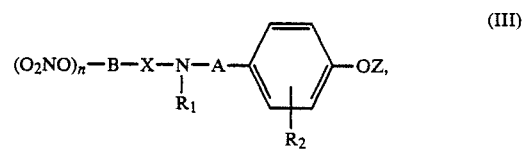

in which A, B, X, R$_1$, R$_2$ and n have the above-given meanings and Z is the group

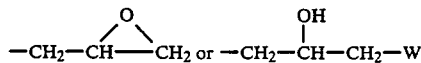

in which W is a reactive group, is reacted with an amine of the general formula:

$$H_2N-R_3 \quad (IV),$$

in which $R_3$ has the above-given meaning; or
(c) a compound of the general formula:

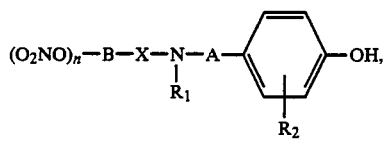

in which A, B, X, $R_1$, $R_2$ and n have the above-given meanings, is reacted with
(c.1) a compound of the general formula:

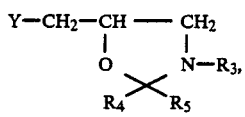

in which $R_3$ has the above-given meaning, Y is a halogen atom or a mesyloxy or tosyloxy radical, $R_4$ is a hydrogen atom or an alkyl radical and $R_5$ independently is a hydrogen atom or an alkyl or phenyl radical or $R_4$ and $R_5$ together with the neighbouring carbon atom, form a carbonyl radical; or
(c.2) a compound of the general formula:

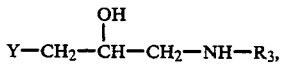

in which Y and $R_3$ have the above-given meanings; or
(d) a compound of the general formula:

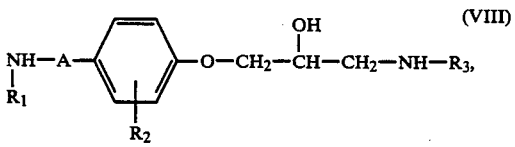

in which A, $R_1$, $R_2$ and $R_3$ have the above-given meanings, is reacted with a compound of the general formula:

$$(O_2NO)_n\text{—}B\text{—}X\text{—}W \quad (IX),$$

in which B, W, X and n have the above-given meanings; or
(e) a compound of the general formula:

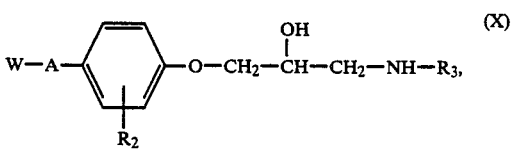

in which A, $R_2$, $R_3$ and W have the above-given meanings, is reacted with a compound of the general formula:

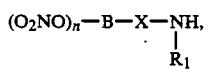

in which B, $R_1$, X and n have the above-given meanings; and, if desired, the compounds so obtained are converted into their physiologically acceptable salts.

The compounds of general formula (II)(intermediates for the preparation of compounds of general formula (I)) are also new and the subject of the present invention. They can be prepared in that, in known manner, a compound of the general formula:

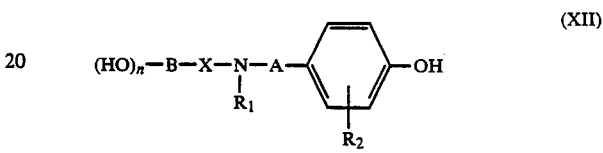

in which A, B, $R_1$, $R_2$, X and n have the above-given meanings
(a) is reacted in an etherification reaction to give a compound of the general formula:

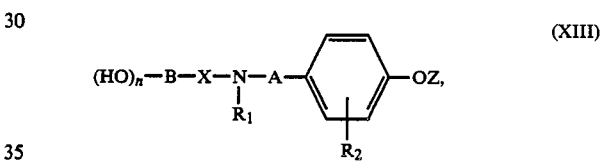

in which A, B, $R_1$, $R_2$, Z, X and n have the above-given meanings, and this converted by reaction with an amine of general formula (IV) into a compound of general formula (II);
(b.1) is reacted with a compound of general formula (VI); or
(b.2) with a compound of general formula (VII); or
(c) a compound of general formula (VIII) is reacted with a compound of the general formula:

$$(HO)_n\text{—}B\text{—}X\text{—}W \quad (XIV),$$

in which B, W, X and n have the above-given meanings; or
(d) a compound of general formula (X) is reacted with a compound of the general formula:

in which B, $R_1$, X and n have the above-given meanings.

The compounds of general formula (III)(intermediates for the preparation of compounds of general formula (I)) are also new and the subject of the present invention. They can be prepared in that, in known manner,
(a) a compound of general formula (XIII) is subjected to a nitrate ester formation reaction; or
(b) a compound of general formula (V) is subjected to a glycide ether or halohydrin formation reaction; or
(c.1) a compound of the general formula:

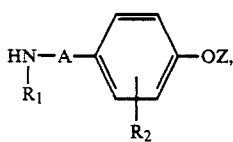

(XVI)

in which A, R₁, R₂ and Z have the above-given meanings, is reacted with a compound of general formula (IX); or (c.2) a compound of the general formula:

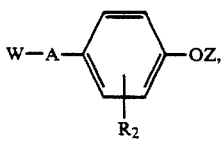

(XVII)

in which A, R₂, W and Z have the above-given meanings, is reacted with a compound of general formula (XI); or (d) a compound of the general formula:

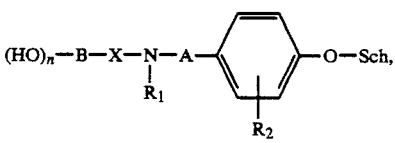

(XVIII)

in which A, B, R₁, R₂, X and n have the above-given meanings and Sch is a protective group, such as an alkoxycarbonyl or tetrahydropyranyl radical, is subjected to a nitrate ester formation reaction, the protective group is subsequently split off and the compound so obtained of general formula (V) is subjected to a glycide ether or halohydrin formation reaction.

The compounds of general formula (V)(intermediates for the preparation of compounds of general formula (I)) are also new and the subject of the present invention. They can be prepared in that, in known manner (a) a compound of general formula (XII) is subjected to a nitrate ester formation reaction; or (b) a compound of the general formula:

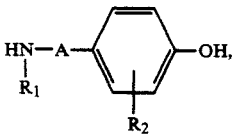

(XIX)

in which A, R₁ and R₂ have the above-given meanings, is reacted with a compound of the general formula (IX); or (c) a compound of the general formula:

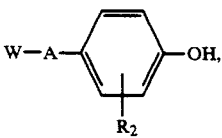

(XX)

in which A, R₂ and W have the above-given meanings, is reacted with a compound of general formula (XI).

The nitrate ester formation reactions of the compounds of general formulae (II), (XII), (XIII), (XV) and (XVIII) can be carried out by reacting a compound of the general formulae (II), (XII), (XIII), (XV) and (XVIII) with a nitrate ester-forming reagent, such as fuming nitric acid, a mixture of fuming nitric acid and acetic anhydride or a mixture of fuming nitric acid and concentrated sulphuric acid, at a low temperature in the presence or absence of an inert solvent. The reaction temperature is from ambient temperature to −60° C. and preferably from −10° C. to −30° C. The mole ratio of the reaction components is from 1 to 10.

Alternatively, the nitrate ester formation reaction can be carried out by selectively halogenating an aliphatic hydroxyl group in a compound of general formula (II), (XII), (XIII), or (XVIII) and subsequently reacting the reaction product with silver nitrate in the presence or absence of a solvent at a temperature of from ambient temperature to 100° C. The mole ratio in the reaction between the halogen compound and the silver nitrate can be from 1 to 10.

The halogenation reaction can be carried out by processes known from the literature by reacting a compound of general formula (II), (XII), (XIII) or (XVIII) with mesyl chloride or tosyl chloride in the presence of an acid-binding agent and subsequently reacting the reaction product with an alkali metal halide in an organic solvent, for example dimethylformamide.

The preparation of compounds of general formulae(III), (XIII) and (XVI) takes place in known manner by reacting an epihalohydrin in an organic solvent and/or water in the presence of an acid-binding agent, such as an alkali metal hydroxide or hydride or an organic nitrogen base, with a compound of general formula (V) or (XII) or of the general formula:

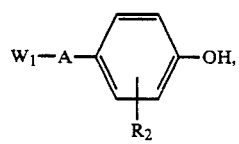

(XXI)

in which A has the above-given meaning and W₁ is an NO₂ group or an alkylcarbonylamino radical, at a temperature of from ambient temperature to 100° C. and, if desired, the group W₁ is converted into a —HN(R₁)— group. The mole ratio of the compound of general formula (V), (XII) or (XXI) to the epihalohydrin can be from 1 to 100.

The reaction of compounds of general formulae (V), (XII) and (XXI) with compounds of general formulae (VI) or (VII) takes place in an organic solvent, for example methanol, ethanol, propanol, benzene, toluene or dimethylformamide, at a temperature of from ambient temperature to 100° C. The mole ratio can be from 1 to 10.

The reaction of compounds of general formulae (III), (XIII) and (XVI) with an amine of general formula (IV) takes place in the presence or absence of a solvent at a temperature of from 0° to 90° C. and preferably of from 20° to 50° C. As solvent, there can be used, for example, methanol, ethanol, propanol, isopropanol, benzene, toluene or dimethylformamide. The molar ratio of the reaction components is not critical: ratios of from 2 to 100 can be used.

The reaction of the amines of general formulae (VIII), (XVI) and (XIX) with activated compounds of general formulae (IX) and (XIV) is carried out in an organic solvent, such as hexane, diethyl ether, tetrahydrofuran, methylene chloride, benzene, toluene or dimethylformamide, or in aqueous solution at a temperature of from $-50°$ C. to $+70°$ C. and preferably of from $-30°$ C. to ambient temperature.

The activated compounds of general formulae (IX) and (XIV) can thereby be present, for example, in the form of carboxylic acid halides, anhydrides or esters or the activation of the carboxylic acids can take place by means of activating reagents, such as N,N'-carbonyldiimidazole, N,N'-dicyclohexylcarbodiimide, 1-ethyl-3-(3-dimethylaminopropyl)-carbodiimide, 1-alkyl-2-halogenopyridinium salts and the like. The activation and the reaction with the amines of general formulae (VIII), (XVI) and (XIX) can thereby be carried out in one synthesis step. Molar ratios of from 1 to 10 can be used.

The reaction of the amines of general formulae (XI) and (XV) with activated compounds of general formulae (X), (XVII) and (XX) are carried out in an organic solvent, such as diethyl ether, tetrahydrofuran, dioxan, methylene chloride, benzene, toluene or dimethylformamide, or in water at a temperature of from $-50°$ C. to $+100°$ C. and preferably of from $-30°$ C. to ambient temperature. The activated compounds of general formulae (X), (XVII) and (XX) can thereby be present, for example, in the form of carboxylic acid halides, anhydrides or esters or the activation can take place in the reaction mixture with activating reagents, such as N,N'-carbonyldiimidazole, N,N'-dicyclohexylcarbodiimide or 1-ethyl-3-(3-dimethylaminopropyl)-carbodiimide. The activation and the reaction with the amines of general formulae (XI) and (XV) can thereby take place in one step. The molar ratio of the reaction components is not critical; ratios of from 1 to 10 can be used.

The compounds according to the present invention possess asymmetric carbon atoms. Therefore, the present invention includes all possible diastereoisomeric mixtures, racemates and all optically-active forms of the compounds according to the present invention of general formulae (I), (II), (III) and possibly also (V).

For the conversion of compounds of general formulae (I)and (II) into their pharmacologically acceptable salts, these are reacted, preferably in an organic solvent, with an equivalent amount of an inorganic or organic acid, for example, hydrochloric acid, hydrobromic acid, nitric acid, phosphoric acid, sulphuric acid, formic acid, acetic acid, propionic acid, oxalic acid, fumaric acid, maleic acid, succinic acid, adipic acid, benzoic acid, salicylic acid, o-acetoxybenzoic acid, cinnamic acid, naphthoic acid, mandelic acid, citric acid, malic acid, tartaric acid, aspartic acid, glutamic acid, methanesulphonic acid or p-toluenesulphonic acid.

The new compounds of general formulae (I) and (II) according to the present invention and the salts thereof can be administered enterally or parenterally in liquid or solid form. As injection medium, water is preferably used which contains the additives usual in the case of injection solutions, such as stabilising agents, solubilising agents or buffers. Additives of this kind include, for example, tartrate and citrate buffers, ethanol, complex forming agents (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (for example polyethylene glycols). Compositions which are suitable for oral administration can, if desired, contain flavouring and sweetening materials.

The compounds according to the present invention are usually administered in amounts of from 20 to 500 mg. per day, referred to a body weight of 75 kg. It is preferred to administer, 2 to 3 times a day, 1 to 2 tablets with an active material content of from 10 to 200 mg. The tablets can also be retarded, in which case 1 to 2 tablets containing 20 to 500 mg. of active material have to be given once per day. The active materials can also be administered by injection 1 to 8 times a day or by continuous infusion, in which case amounts of active material of from 5 to 200 mg./day normally suffice.

Besides the compounds described in the Examples, the following compounds are also preferred according to the present invention:

1-[4-(2-methyl-1-nitroxy-2-propyl)-carbonylamino]-phenoxy-3-isopropylaminopropan-2-ol 3-(2-methyl-2-butyn-2-yl)-amino-1-[4-(2-methyl-1-nitroxy-2-propyl)-carbonylamino]-phenoxypropan-2-ol 3-isopropylamino-1-[4-[[(t-4-nitroxy)-cyclohexyl]-r-1-carbonylamino]]-phenoxypropan-2-ol 3-(2-methyl-3-butyn-2-yl)-amino-1-[4-[[(t-4-nitroxy)cyclohexyl]-r-1-carbonylamino]]-phenoxypropan-2-ol 3-isopropylamino-1-[4-[[(t-2-nitroxy)-cyclohexyl]-r-1-methylcarbonylamino]]-phenoxypropan-2-ol 3-(2-methyl-3-butyn-2-yl)-amino-1-[4-[[(t-2-nitroxy)cyclohexyl]-r-1-methylcarbonylamino]]-phenoxypropan-2-ol 1-[2-cyano-4-(3-nitroxypropyl)-carbonylamino]-phenoxy-3-isopropylaminopropan-2-ol 1-[2-cyano-4-(3-nitroxypropyl)-carbonylamino]-phenoxy-3-(2-methyl-3-butyn-2-yl)-aminopropan-2-ol 1-[2-cyano-4-[[(t-4-nitroxy)-cyclohexyl]-r-1-carbonylamino]]-phenoxy-3-isopropylaminopropan-2-ol 1-[2-cyano-4-[[(t-4-nitroxy)-cyclohexyl]-r-1-carbonylamino]]-phenoxy-3-(2-methyl-3-butyn-2-yl)-aminopropan-2-ol 3-isopropylamino-1-[2-methylcarbonyl-4-(3-nitroxypropyl)carbonylamino]-phenoxypropan-2-ol 3-(2-methyl-3-butyn-2-yl)-amino-1-[2-methylcarbonyl-4-(3-nitroxypropyl)-carbonylamino]-phenoxypropan-2-ol 3-isopropylamino-1-[2-methylcarbonyl-4-[[(t-4-nitroxycyclohexyl]-r-1-carbonylamino]]-phenoxypropan-2-ol 3-(2-methyl-3-butyn-2-yl)-amino-1-[2-methylcarbonyl-4-[[(t-4-nitroxy)-cyclohexyl]-r-1-carbonylamino]]-phenoxypropan-2-ol 1-[ethoxycarbonyl-4-(4-nitroxybutyl)-carbonylamino]-phenoxy-3-tert.-butylaminopropan-2-ol 1-[2-ethoxycarbonyl-4-(2-methyl-1-nitroxy-2-propyl)-carbonylamino]-phenoxy-3-tert.-butylaminopropan-2-ol 1-[2-ethoxycarbonyl-4-[[(t-4-nitroxy)-cyclohexyl-r-1-carbonylamino]]-phenoxy-3-tert.-butylaminopropan-2-ol 1-[2-ethoxycarbonyl-4-[[[(t-2-nitroxy)-cyclohexyl]-r-1-methyl]-carbonyl]-amino]-phenoxy-3-tert.-butylaminopropan-2-ol 1-[2-ethoxycarbonyl-4-(3-nitroxypropyl)-carbonylamino]phenoxy-3-isopropylaminopropan-2-ol 1-[2-ethoxycarbonyl-4-(3-nitroxypropyl)-carbonylamino]phenoxy-3-(2-methyl-3-butyn-2-yl)-aminopropan-2-ol
1-[4-[(2-nitroxyethyl)-amino]-carbonylmethyl]-phenoxy-3-tert.-butylaminopropan-2-ol
1-[4-[(1-nitroxybut-3-yl)-amino]-carbonylmethyl]-phenoxy-3-tert.-butylaminopropan-2-ol
1-[4-[(2-methyl-4-nitroxy-2-butyl)-amino]-carbonylmethyl]phenoxy-3-tert.-butylaminopropan-2-ol
1-[4-[(2,3-dinitroxypropyl)-amino]-carbonylmethyl]-phenoxy-3-tert.-butylaminopropan-2-ol
1-[4-[N,N-bis-(2-nitroxyethyl)-amino]-carbonylmethyl]-phenoxy-3-tert.-butylaminopropan-2-ol
1-[4-[N,N-bis-(2-nitroxypropyl)-amino]-carbonylmethyl]phenoxy-3-tert.-butylaminopropan-2-ol
trans-1-[4-[(4-nitroxycyclohexyl)-amino]-carbonylmethyl]phenoxy-3-tert.-butylaminopropan-2-ol
3-isopropylamino-1-[4-[(3-nitroxypropyl)-amino]-carbonylmethyl]-phenoxypropan-2-ol
3-isopropylamino-1-[4-[(2-nitroxypropyl)-amino]-carbonylmethyl]-phenoxypropan-2-ol
3-isopropylamino-1-[4-[1-nitroxybut-3-yl)-amino]-carbonylmethyl]-phenoxypropan-2-ol
3-isopropylamino-1-[4-[(2-methyl-4-nitroxy-2-butyl)-amino]carbonylmethyl]-phenoxypropan-2-ol
3-isopropylamino-1-[4-[(2,2-dimethyl-3-nitroxypropyl)amino]-carbonylmethyl]-phenoxypropan-2-ol
3-isopropylamino-1-[4-[(2,3-dinitroxypropyl)-amino]-carbonylmethyl]-phenoxypropan-2-ol
3-isopropylamino-1-[4-[[N-methyl-N-(3-nitroxypropyl)-]amino]-carbonylmethyl]-phenoxypropan-2-ol
3-isopropylamino-1-[4-[[N-methyl-N-(2-nitroxypropyl)-]amino]-carbonylmethyl]-phenoxypropan-2-ol
3-isopropylamino-1-[4-[[N-methyl-N-(4-nitroxybutyl)-]amino]-carbonylmethyl]-phenoxypropan-2-ol
3-isopropylamino-1-[4-[[N-methyl-N-(1-nitroxybut-3-yl)]amino]-carbonylmethyl]-phenoxypropan-2-ol
3-isopropylamino-1-[4-[[N-methyl-N-(2,2-dimethyl-3-nitroxypropyl)]-amino]-carbonylmethyl]-phenoxypropan-2-ol
trans-3-isopropylamino-1-[4-[(2-nitroxycyclohexyl)-amino]carbonylmethyl]-phenoxypropan-2-ol
trans-3-isopropylamino-1-[4-[(4-nitroxycyclohexyl)-amino]carbonylmethyl]-phenoxypropan-2-ol
cis-3-isopropylamino-1-[4-[(4-nitroxycyclohexyl)-amino]carbonylmethyl]-phenoxypropan-2-ol
trans-3-isopropylamino-1-[4-[[(4-nitroxycyclohexyl)methyl]-amino]-carbonylmethyl]-phenoxypropan-2-ol
trans-3-isopropylamino-1-[4-[[(2-nitroxycyclohexyl)methyl]-amino]-carbonylmethyl]-phenoxypropan-2-ol
3-isopropylamino-1-[4-(4-nitroxy-1-piperidino)-carbonylmethyl]-phenoxypropan-2-ol
3-isoproylamino-1-[4-(2-nitroxymethyl-1-piperidino)-carbonylmethyl]-phenoxypropan-2-ol
3-isopropylamino-1-[4-(3-nitroxymethyl-1-piperidino)-carbonylmethyl]-phenoxypropan-2-ol
3-(2-methyl-3-butyn-2-yl)-amino-1-[4-[(3-nitropropyl)amino]-carbonylmethyl]-phenoxypropan-2-ol
3-(2-methyl-3-butyn-2-yl)-amino-1-[4-[(2-nitroxypropyl)amino]-carbonylmethyl]-phenoxypropan-2-ol
3-(2-methyl-3-butyn-2-yl)-amino-1-[4-(4-nitroxy-1-piperidino)-carbonylmethyl]-phenoxypropan-2-ol
1-[4-(3-nitroxypropyl)-carbonylamino]-phenoxy-3-isopropylaminopropan-2-ol
1-[4-(3-nitroxypropyl)-carbonylamino]-phenoxy-3-(2-methyl-3-butyn-2-yl)-aminopropan-2-ol
1-[4-[2-(3-nitroxypropyl)-carbonylamino]-ethyl]-phenoxy-3-tert.-butylaminopropan-2-ol
1-[4-[2-(2-methyl-1-nitroxy-2-propyl)-carbonylamino]ethyl]-phenoxy-3-tert.-butylaminopropan-2-ol
1-[4-[[N-methyl-N-(3-nitroxypropyl)]-amino]-carbonylmethyl]phenoxy-3-tert.-butylaminopropan-2-ol
1-[4-[[N-methyl-N-(2-nitroxypropyl)]-amino]-carbonylmethyl]phenoxy-3-tert.-butylaminopropan-2-ol
1-[4-[[N-methyl-N-(4-nitroxybutyl)]-amino]-carbonylmethyl]phenoxy-3-tert.-butylaminopropan-2-ol
1-[4-[[N-methyl-N-(1-nitroxybut-3-yl)]-amino]-carbonylmethyl]-phenoxy-3-tert.-butylaminopropan-2-ol
cis-1-[4-[(4-nitroxycyclohexyl)-amino]-carbonylmethyl]phenoxy-3-tert.-butylaminopropan-2-ol
1-[4-(2-nitroxymethyl-1-piperidino)-carbonylmethyl]-phenoxy-3-tert.-butylaminopropan-2-ol
1-[4-[(2-nitroxyethylthio)-methylcarbonylamino]-phenoxy]-3-tert.-butylaminopropan-2-ol
1-[4-[(2-nitroxyethylsulphinyl)-methylcarbonylamino]-phenoxy]-3-tert.-butylaminopropan-2-ol
1-[4-[(2-nitroxyethylsulphonyl)-methylcarbonylamino]-phenoxy]-3-tert.-butylaminopropan-2-ol.

The following Examples are given for the purpose of illustrating the present invention.

EXAMPLE 1

1-[4-(3-Nitroxypropyl)-carbonylamino]-phenoxy-3-tert.-butylaminopropan-2-ol hydrochloride A solution of 3.6 g. 4-nitroxybutanoyl chloride is added dropwise to a solution of 5.0 g. 1-(4-aminophenoxy)-3-tert.-butylaminopropan-2-ol in 100 ml. dry tetrahydrofuran at ambient temperature. The reaction mixture is stirred for 1 hour at ambient temperature and then evaporated to dryness in a vacuum. The residue obtained is triturated with a little diethyl ether and the precipitate obtained is filtered off with suction and dried. There are obtained 7.1 g. (83% of theory) of the title compound in the form of crystals; m.p. 137°-140° C.

The 4-nitroxybutanoyl chloride required as starting material is prepared as follows:

2.08 g. Phosphorus pentachloride are added at ambient temperature to a solution of 1.49 g. N-nitroxybutyric acid in 150 ml. dry methylene chloride. The reaction mixture is stirred for 1 hour and then the solvent is stripped off in a vacuum. The residue obtained (1.7 g. of oil) is further reacted directly.

The 1-(4-aminophenoxy)-3-tert.-butylaminopropan-2-ol needed as starting material, as well as 1-(4-aminophenoxy)-3-isopropylaminopropan-2-ol and 1-(4-aminophenoxy)-3-(2-methyl-3-butyn-2-yl)-aminopropan-2-ol are prepared according to known processes and according to the processes described in European Patent Specification No. 0,029.992.

The 4-nitroxybutyric acid needed as starting material is prepared in known manner from sodium 4-hydroxybutanoate and a mixture of 100% nitric acid/96% sulphuric acid. The other nitroxyalkylcarboxylic acids are prepared analogously from the appropriate hydroxyalkylcarboxylic acids.

EXAMPLE 2

In a manner analogous to that described in Example 1, from 1-(4-aminophenoxy)-3-tert.-butylaminopropan-2-ol, 1-(4-aminophenoxy)-3-isopropylaminopropan-2-ol and 1-(4-aminophenoxy)-3-(2-methyl-3-butyn-2-yl)-aminopropan-2-ol and the appropriate nitroxyalkylcarboxylic acid chlorides, there are obtained the following compounds:

| designation | yield % | m.p. in °C. (solvent) |
|---|---|---|
| (a) 1-[4-(4-nitroxybutyl)-carbonyl-amino]-phenoxy-3-tert.-butyl-aminopropan-2-ol fumarate from 5-nitroxypentanoyl chloride | 41 | 128–130 (ethyl acetate) |
| (b) 1-[4-(2-methyl-1-nitroxy-2-propyl)-carbonylamino]-phenoxy-3-tert.-butylaminopropan-2-ol hydrochloride from 2,2-dimethyl-3-nitroxypropionyl chloride (pale yellow oil) | 78 | 149–150 (ethyl acetate) |
| (c) 1-[4-[1,1-bis-(nitroxymethyl)-ethyl]-carbonylamino]-phenoxy-3-tert.-butylaminopropan-2-ol hydrochloride from 2,2-bis-(nitroxymethyl)-propionyl chloride (colourless oil) | 90 | 97–100 (diethyl ether) |
| (d) 1-[4-[[(t-3,t-4-dinitroxy)-cyclopentyl]-r-1-carbonylamino]]-phenoxy-3-tert.-butylamino-propan-2-ol fumarate from (t-3,t-4-dinitroxy)-cyclopentane-carboxylic acid chloride (colourless oil) | 72 | 198–199 (diethyl ether) |
| (e) 1-[4-[[(t-4-nitroxy)-cyclo-hexyl]-r-1-carbonylamino]]-phenoxy-3-tert.-butylamino-propan-2-ol hydrochloride from trans-4-nitroxycyclohexane-carboxylic acid chloride (pale yellow oil | 97 | 104–106 (diethyl ether) |
| (f) 1-[4-[[(t-3,c-4-dinitroxy)-cyclohexyl]-r-1-carbonylamino]]-phenoxy-3-tert.-butylaminopropan-2-ol hydrochloride from (t-3,c-4-dinitroxy)-cyclohexane-carboxylic acid chloride (colourless oil) | 100 | 77–80 (diethyl ether) |
| (g) 1-[4-[[(t-2-nitroxy)-cyclo-hexyl]-r-1-methylcarbonylamino]]-phenoxy-3-tert.-butylamino-propan-2-ol hydrochloride from trans-2-(2-nitroxycyclohexyl)-acetyl chloride (colourless oil) | 57 | 115–118 (ethyl acetate) |
| (h) 1-[4-[[(2-nitroxymethoxy)-methyl]-carbonylamino]-phenoxy]-3-tert.-butylaminopropan-2-ol fumarate from 2-nitroxyethoxyacetyl chloride | 32 | 166–167 (ethyl acetate) |

EXAMPLE 3

1-[2-Cyano-4-(2-methyl-1-nitroxy-2-propyl)-carbonylamino]phenoxy-3-tert.-butylaminopropan-2-ol benzoate A solution of 2.0 g. 2,2-dimethyl-3-nitroxypropionyl chloride in 50 ml. dry methylene chloride is added dropwise at 5° C. to a suspension of 2.6 g. 1-(4-amino-2-cyanophenoxy)-3-tert.-butylaminopropan-2-ol in 50 ml. dry methylene chloride, the reaction mixture is stirred for a further 2 hours at 5° C. and allowed to come to ambient temperature overnight. The reaction mixture is then mixed with 100 ml. aqueous potassium carbonate solution and extracted 5 times with, in each case, 100 ml. methylene chloride. The extracts are dried over anhydrous sodium sulphate, the residue is dissolved in ethyl acetate/diethyl ether and extracted with aqueous lactic acid solution. The aqueous phase is then extracted 3 times with ethyl acetate. The combined organic phases are dried over anhydrous sodium sulphate and then evaporated. The residue obtained (3.5 g.) is dissolved in ethyl acetate and mixed with 0.8 g. benzoic acid. The precipitate obtained is filtered off with suction and dried. There are obtained 3.2 g. (61% of theory) of the title compound in the form of crystals; m.p. 131°–133° C.

The 1-(4-amino-2-cyanophenoxy)-3-tert.-butylaminopropan-2-ol required as starting material is prepared according to known processes and according to the instructions given in European Patent Specification No. 0,029,992.

EXAMPLE 4

In a manner analogous to that described in Example 3, from 1-(4-amino-2-cyanophenoxy)-3-tert.-butylaminopropan-2-ol and the appropriate nitroxyalkylcarboxylic acid chlorides, there are obtained the following compounds:

| designation | yield % | m.p. in °C. (solvent) |
|---|---|---|
| (a) 1-[2-cyano-4-(3-nitroxypropyl)-carbonylamino]-phenoxy-3-tert.-butylaminopropan-2-ol hydrochloride from 4-nitroxybutanoyl chloride | 63 | amorphous |
| (b) 1-[2-cyano-4-[1,1-bis-(nitroxymethyl)-ethyl]-carbonylamino]-phenoxy-3-tert.-butylaminopropan-2-ol benzoate from 2,2-bis-(nitroxmethyl)-propionyl chloride | 40 | 50 (diethyl ether) |
| (c) 1-[2-cyano-4-[[(t-4-nitroxy)-cyclohexyl]-r-1-carbonylamino]]-phenoxy-3-tert.-butylamino-propan-2-ol benzoate from trans-4-nitroxycyclohexane-carboxylic acid chloride | 73 | 154–156 (ethyl acetate) |
| (d) 1-[2-cyano-4-[[(t-3,c-4-dinitroxy)-cyclohexyl]-r-1-carbonylamino]]-phenoxy-3-tert.-butylaminopropan-2-ol benzoate from (t-3,c-4-dinitroxy)-cyclohexane-carboxylic acid chloride | 38 | 148 (ethyl acetate) |
| (e) 1-[2-cyano-4-[[(t-2-nitroxy)-cyclohexyl]-r-1-methylcarbonylamino]]-phenoxy-3-tert.-butyl-aminopropan-2-ol benzoate from trans-2-(2-nitroxycyclohexyl)-acetyl chloride | 60 | 148–149 (ethyl acetate) |

EXAMPLE 5

1-[4-(2-Methyl-1-nitroxy-2-propyl)-carbonylamino-2-methylcarbonyl]-phenoxy-3-tert.-butylaminopropan-2-ol hydrochloride A solution of 2.7 g. 2,2-dimethyl-3-nitroxypropionyl chloride in 70 ml. dry tetrahydrofuran is added dropwise at ambient temperature to a solution of 3.4 g. 1-(4-amino-2-methylcarbonyl)-phenoxy-3-tert.-butylaminopropan-2-ol in 70 ml. dry tetrahydrofuran. The reaction mixture is stirred overnight, the crystals obtained are filtered off with suction and dried. There are obtained 4.9 g. (88% of theory) of title compound in the form of crystals; m.p. 175°–177° C.

The 1-(4-amino-2-methylcarbonyl)-phenoxy-3-tert.-butylaminopropan-2-ol needed as starting material is prepared according to known processes and according to the instructions given in European patent specification No. 0,029,992.

EXAMPLE 6

In a manner analogous to that described in Example 5, from 1-(4-amino-2-methylcarbonyl)-phenoxy-3-tert.-butylaminopropan-2-ol and the appropriate nitroxyalkylcarboxylic acid chlorides, there are obtained the following compounds:

| designation | yield % | m.p. in °C. (solvent) |
| --- | --- | --- |
| (a) 1-[2-methylcarbonyl-4-(3-nitroxypropyl)-carbonylamino]-phenoxy-3-tert.-butylaminopropan-2-ol fumarate from 4-nitroxybutanoyl chloride | 63 | 63–65 (amorphous) (ethyl acetate) |
| (b) 1-[4-(1,1-bis-(nitroxymethyl)-ethyl]-carbonylamino-2-methylcarbonyl]-phenoxy-3-tert.-butylaminopropan-2-ol hydrochloride from 2,2-bis-(nitroxymethyl)-propionyl chloride | 69 | 141–142 (ethyl acetate) |
| (c) 1-[2-methylcarbonyl-4-[[(t-4-nitroxy)-cyclohexyl]-r-1-carbonylamino]]-phenoxy-3-tert.-butylaminopropan-2-ol hydrochloride from trans-4-nitroxycyclohexanecarboxylic acid chloride | 91 | 135–137 (tetrahdrofuran) |
| (d) 1-[4-[[(t-3,c-4-dinitroxy)-cyclohexyl]-r-1-carbonylamino-2-methylcarbonyl]-phenoxy-3-tert.-butylaminopropan-2-ol hydrochloride from (t-3,c-4-ninitroxy)-cyclohexanecarboxylic acid chloride | 97 | 165–167 (tetrahydrofuran) |
| (e) 1-[2-methylcarbonyl-4-[[(t-2-nitroxy)-cyclohexyl]-r-1-methylcarbonylamino]]-phenoxy-3-tert.-butylaminopropan-2-ol hydrochloride from trans-2-(2-nitroxycyclohexyl)-acetyl chloride | 66 | 132–134 (acetone) |

EXAMPLE 7

1-[2-Ethoxycarbonyl-4-(3-nitroxypropyl)-carbonylamino]phenoxy-3-tert.-butylaminopropan-2-ol cyclamate 3 ml. Triethylamine are added to a solution of 6.85 g. 1-(4-amino-2-ethoxycarbonyl)-phenoxy-3-tert.-butylaminopropan-2-ol in 250 ml. dry tetrahydrofuran and at 10° C. a solution of 3.6 g. 4-nitroxybutanoyl chloride in 30 ml. dry tetrahydrofuran is added dropwise thereto. The reaction mixture is stirred for 10 hours at this temperature, precipitate is filtered off with suction and the filtrate is evaporated to dryness. The residue obtained (8.4 g.) is dissolved in 150 ml. methylene chloride and extracted three times with 150 ml. amounts of water. The aqueous phases are saturated with sodium chloride and extracted three times with 150 ml. amounts of ethyl acetate. The ethyl acetate phases are dried and evaporated. The residue obtained (3.9 g.) is dissolved in 30 ml. ethyl acetate and mixed with a solution of 1.59 g. cyclamic acid in 60 ml. ethyl acetate. The crystals which separate out are filtered off with suction and dried. There are obtained 1.8 g. (13% of theory) of the title compound in the form of crystals; m.p. 118°–120° C.

The 1-(4-amino-2-ethoxycarbonyl)-phenoxy-3-tert.-butylaminopropan-2-ol needed as starting material is prepared according to known processes and according to the instructions given in European patent specification No. 0,029,992.

EXAMPLE 8

1-[4-[(3-Nitroxypropyl)-amino]-carbonylmethyl]-phenoxy-3-tert.-butylaminopropan-2-ol fumarate.

26.5 ml. tert.-Butylamine are added to 13.4 g. 2,3-epoxy-1-[4-[(3-nitroxypropyl)-amino]-carbonylmethyl]-phenoxypropane and the reaction mixture is stirred for 15 hours at ambient temperature. Excess amine is then stripped off in a vacuum, the residue is dissolved in 150 ml. methylene chloride, washed twice with 30 ml. amounts of saturated aqueous sodium chloride solution, then twice with 50 ml. amounts of 0.01N hydrochloric acid and again with 30 ml. of saturated aqueous sodium chloride solution, purified with active charcoal, dried and evaporated. The remaining residue (12.8 g.) is dissolved in 150 ml. ethyl acetate and mixed with a solution of 3.9 g. fumaric acid in 200 ml. acetone. The oil which separates out is decanted off, mixed with 200 ml. diethyl ether and stirred for 12 hours at ambient temperature. The crystallised salt is filtered off with suction and dried. There are obtained 13.2 g. (61% of theory) of the title compound in the forms of crystals; m.p. 98°–100° C.

EXAMPLE 9

In a manner analogous to that described in Example 8, from 2,3-epoxy-1-[4-[(nitroxy)-amino]-carbonylmethyl]-phenoxypropanes and primary amines, there are obtained the following compounds:

| designation | yield % | m.p. in °C. (solvent) |
| --- | --- | --- |
| (a) 1-[4-[(2-nitroxypropyl)-amino]-carbonylmethyl]-phenoxy-3-tert.-butylaminopropan-2-ol hemifumarate from 2,3-epoxy-1-[4-[(2-nitroxypropyl)-amino]-carbonylmethyl]-phenoxypropane and tert.-butylamine | 50 | 78–79 (diethyl ether) |
| (b) 1-[4-[(2,2-dimethyl-3-nitroxypropyl)-amino]-carbonylmethyl]-phenoxy-3-tert.-butylaminopropan-2-ol fumarate from 2,3-epoxy-1-[4-[(2,2-dimethyl-3-nitroxypropyl)-amino]-carbonylmethyl]-phenoxypropane and tert.-butylamine | 60 | 180–182 (diethyl ether) |
| (c) 1-[4-[[N—(2,2-dimethyl-3-nitroxypropyl)-N—methyl]-amino]-carbonylmethyl]-phenoxy-3-tert.-butylaminopropan-2-ol fumarate from 1-[4-[[N—(2,2-dimethyl-3-nitroxypropyl)-N—methyl]-amino]-carbonylmethyl]-phenoxy-2,3-epoxypropane and tert.-butylamine | 57 | 140–142 (acetone) |
| (d) trans-1-[4-[(2-nitroxycyclohexyl)-amino]-carbonylmethyl]-phenoxy-3-tert.-butylaminopropan-2-ol from trans-2,3-epoxy-1-[4-[(2-nitroxycyclohexyl)-amino]-carbonylmethyl]-phenoxypropane and tert.-butylamine | 26 | 103–105 (diethyl ether) |
| (e) trans-1-[4-[[(2-nitroxycyclohexyl)-methyl]-amino]-carbonylmethyl]-phenoxy-3-tert.-butylaminopropan-2-ol benzoate from trans-2,3-epoxy-1-[4-[[4-nitroxycyclohexyl)-methyl]-amino]-carbonylmethyl]-phenoxypropane and tert.-butylamine | 18 | 110–112 (diethyl ether) |

-continued

| designation | yield % | m.p. in °C. (solvent) |
|---|---|---|
| (f) 1-[4-(4-nitroxy-1-piperidino)-carbonylmethyl]-phenoxy-3-tert.-butylaminopropan-2-ol fumarate from 2,3-epoxy-1-[4-(4-nitroxy-1-piperidino)-carbonylmethyl]-phenoxypropane and tert.-butylamine | 34 | 88–90 (diethyl ether) |
| (g) 1-[4-(3-nitroxymethyl-1-piperidino)-carbonylmethyl]-phenoxy-3-tert.-butylaminopropan-2-ol fumarate from 2,3-epoxy-1-[4-(3-nitroxymethyl-1-piperdino)-carbonylmethyl]-phenoxypropane and tert.-butylamine | 47 | 88–90 (diethyl ether) |
| (h) 1-[4-(4-nitroxymethyl-1-piperidino)-carbonylmethyl]-phenoxy-3-tert.-butylaminopropan-2-ol fumarate from 2,3-epoxy-1-[4-(4-nitroxymethyl-1-piperidino)-carbonylmethyl]-phenoxypropane and tert.-butylamine | 67 | 97–99 (diethyl ether) |
| (i) 3-isopropylamino-1-[4-(4-nitroxymethyl-1-piperidino)-carbonylmethyl]-phenoxypropan-2-ol fumarate from 2,3-epoxy-1-[4-(4-nitroxymethyl-1-piperidino)-carbonylmethyl]-phenoxypropane and isopropylamine | 16 | amorphous |
| (j) 3-(2-methyl-3-butyn-2-yl)-amino-1-[4-(4-nitroxymethyl-1-piperidino)-carbonylmethyl]-phenoxypropan-2-ol fumarate from 2,3-epoxy-1-[4-(4-nitroxymethyl-1-piperidino)-carbonylmethyl]-phenoxypropane and 2-methyl-3-butyn-2-ylamine | 20 | 58–60 (diethyl ether) |

EXAMPLE 10

2,3-Epoxy-1-[4-[(3-nitroxypropyl)-amino]-carbonylmethyl]-phenoxypropane required as starting material is prepared as follows:

16.9 ml. epichlorohydrin is added to a solution of 11.0 g. 4-[(3-nitroxypropyl)-amino]-carbonylmethylphenol in 50 ml. dimethylformamide and then 43.3 ml. 1N aqueous sodium hydroxide solution are added dropwise thereto at 20° to 25° C. The reaction mixture is stirred for 4 hours at ambient temperature and then evaporated to dryness in a vacuum at a bath temperature of 30° C. The residue is mixed with methylene chloride and water. After phase separation, the organic phase is washed twice with water, dried and evaporated. There are obtained 13.4 g. (100% of theory) of the desired product in the form of an oil. This is further worked up directly.

EXAMPLE 11

In a manner analogous to that described in Example 10, the following compounds are prepared from epichlorohydrin and the appropriate 4-(nitroxyalkylamino)-carbonylmethylphenols:

| designation | yield % |
|---|---|
| (a) 2,3-epoxy-1-[4-[(2-nitroxypropyl)-amino]-carbonylmethyl]-phenoxypropane (yellow oil) from 4-[(2-nitroxypropyl)-amino]-carbonylmethylphenol | 90 |
| (b) 2,3-epoxy-1-[4-[(2,2-dimethyl-3-nitroxypropyl)-amino]-carbonylmethyl]-phenoxypropane (colourless oil) from 4-[(2,2-dimethyl-3-nitroxypropyl)-amino]-carbonylmethylphenol | 86 |
| (c) 2,3-epoxy-1-[4-[[N—methyl-N—(2-nitroxypropyl)]-amino]-carbonylmethyl]-phenoxypropane (yellow oil) from 4-[[N—methyl-N—(2-nitroxypropyl)]-amino]-carbonylmethylphenol | 56 |
| (d) 1-[4-[[N—(2,2-dimethyl-3-nitroxypropyl)-N—methyl]-amino]-carbonylmethyl]-phenoxy-2,3-epoxypropane(yellow oil) from 4-[[N—(2,2-dimethyl-3-nitroxypropyl)-N—methyl]-amino]-carbonylmethylphenol | 82 |
| (e) trans-2,3-epoxy-1-[4-(2-nitroxycyclohexyl)-amino]-carbonylmethyl]-phenoxypropane from trans-4-[(2-nitroxycyclohexyl)-amino]-carbonylmethylphenol | 89 |
| (f) trans-2,3-epoxy-1-[4-[[(2-nitroxycyclohexyl)-methyl]-amino]-carbonylmethyl]-phenoxypropane from trans-4-[[(2-nitroxycyclohexyl)-methyl]-amino]-carbonylmethylphenol | 100 |
| (g) 2,3-epoxy-1-[4-(4-nitroxy-1-piperidino)-carbonylmethyl]-phenoxypropane (yellow oil from 4-(4-nitroxy-1-piperidino)-carbonylmethylphenol | 99 |
| (h) 2,3-epoxy-1-[4-(3-nitroxymethyl-1-piperidino)-carbonylmethyl]-phenoxypropane (yellow oil) from 4-(3-nitroxmethyl-1-piperidino)-carbonylmethylphenol | 91 |
| (i) 2,3-epoxy-1-[4-(4-nitroxymethyl-1-piperidino)-carbonylmethyl]-phenoxypropane (colourless oil) from 4-(4-nitroxymethyl-1-piperidino)-carbonylmethylphenol | 100 |

EXAMPLE 12

4-[(3-Nitroxypropyl)-amino]-carbonylmethylphenol required as starting material is prepared as follows:

A solution of 7.6 g. (4-hydroxyphenyl)-acetic acid in 5 ml. dry dimethylformamide and 200 ml. dry methylene chloride is mixed with 5.5 ml. 4-methylmorpholine and cooled to −20° to −15° C. A solution of 6.6 ml. isobutyl chloroformate in 200 ml. dry methylene chloride is added dropwise at this temperature within the course of 45 minutes and stirring continued for 1.5 hours. 9.15 g. 3-nitroxypropylammonium nitrate is then added thereto at −20° to −15° C. and a solution of 5.5 ml. 4-methylmorpholine in 20 ml. dry methylene chloride added dropwise thereto, followed by further stirring for 1 hour. The reaction mixture is allowed to warm up to ambient temperature and then successively washed with 55 ml. 0.2N hydrochloric acid, 50 ml. 5% sodium hydrogen carbonate solution and 50 ml. water, dried over anhydrous sodium sulphate and evaporated. There are obtained 11 g. of the desired product in the form of an oil (87% of theory).

EXAMPLE 13

In a manner analogous to that described in Example 12, the following compounds are obtained from (4-hydroxyphenyl)-acetic acid and the appropriate nitroxyalkylammonium nitrates:

| desigation | yield % |
|---|---|
| (a) 4-[-(2-nitropropyl)-amino]-carbonyl-methylphenol(pale yellow oil) from 2-nitropropylammonium nitrate | 100 |
| (b) 4-[(2,2-dimethyl-3-nitroxypropyl)-amino]-carbonylmethylphenol (pale yellow oil) from (2,2-dimethyl-3-nitroxypropyl)-ammonium nitrate | 100 |
| (c) 4-[[N—methyl-N—(2-nitroxypropyl)]-amino]-carbonylmethylphenol (colourless oil) from N—methyl-N—(-nitroxypropyl)-ammonium nitrate | 72 |
| (d) 4-[[N—(2,2-dimethyl-3-nitroxy-propyl)-N—methyl]-amino]-carbonyl-methylphenol (yellow oil) from N—(2,2-dimethyl-3-nitroxypropyl)-N—methylammonium nitrate | 100 |
| (e) trans-4-[(2-nitroxycyclohexyl)-amino]-carbonylmethylphenol from trans-(2-nitroxycyclohexyl)-ammonium nitrate | 39 |
| (f) trans-4-[[(2-nitroxycyclohexyl)-methyl]-amino]-carbonylmethylphenol from trans-(2-nitroxycyclohexyl)-methyl-ammonium nitrate | 63 |
| (g) 4-(4-nitroxy-1-piperidino)-carbonyl-methylphenol (colourless oil) from 4-nitroxypiperidinium nitrate | 100 |
| (h) 4-(2-nitroxymethyl-1-piperidino)-carbonyl-methylphenol (yellow oil) from 2-nitroxymethylpiperidinium nitrate | 100 |
| (i) 4-(3-nitroxymethyl-1-piperidino)-carbonyl-methylphenol (yellow oil) from 3-nitroxymethylpiperidinium nitrate | 100 |
| (j) 4-(4-nitroxymethyl-1-piperidino)-carbonyl-methylphenol (yellow oil) from 4-nitroxymethylpiperidinium nitrate | 100 |

The nitroxyalkylammonium nitrates required as starting materials are prepared from the corresponding hydroxyalkylamines according to known procedures (see, for example, Houben-Weyl-Müller, Methoden der organischen Chemie, Vol. VI/2, pp 325 et. seq., pub. Georg Thieme Verlag, Stuttgart, 1963).

TEST PROTOCOL

The compounds claimed have beta-blocking as well as nitrate-like properties and can therefore be used as antianginal therapy (heart disorder characterized by attacks of pain where there is an unsufficiency of oxygen).

At present pharmaceuticals are available either for their nitrate-like properties, e.g. nitroglycerin, isosorbide dinitrate, isosorbide-5-mononitrate, or for their beta-blocker properties, e.g. propranolol, pindolol. Combinations of these drugs are also used, but so far no compound is available which by its working principle incorporates both qualities. The invention provides compounds which, surprisingly, have nitrate-like as well as beta-blocking qualities in overlapping dosage ranges. Thus, a single compound can be used to treat two separate (but usually related in occurrence) ailments.

Since such substances have so far not been developed specifically, a method for screening the nitrate-like action is not known. It is for this reason that the following method was developed:

(a) to show denitration properties (which constitutes the working principle of all nitrates; see U. Abshagen in Handbook of Experimental Pharmacology, Vol. 76, 1985, Chapter 10.) the denitration rate was evaluated in relation to that of the known isosorbide dinitrate metabolite isosorbide-5-mononitrate ($V_{rel}$). To that end, rats were killed under narcosis and their livers re-perfused 4 min with a corresponding concentrated equimolar ($5 \times 10^{-5}$ M/l) solution of isosorbide-5-mononitrate and the substances to be tested respectively (a blood sediment solution was pumped through the liver vessels) and the freed amount in $NO_2$ determined in the perfusate (outflowing fluid). To have comparable conditions, the perfusion with isosorbide-5-mononitrate (standard substance) was administered as control at the second time as if it were an unknown substance (in this way a liver performance change under the test conditions can be recognized and accordingly allowed for).

High $V_{rel}$-values show a fast denitration, low values a slow denitration.

(b) The $\beta$-blocking effectiveness was shown by administering rabbits isoprenaline in an amount of 1 mcg/kg i.v. and determining the dose, which causes an inhibition of 50% of the increase of the frequency through isoprenaline (ID $50_{fcor}$=inhibition dose 50%).

TABLE

| Example | ID 50 fcor mcg/kg i.v. | $V_{rel}$ |
|---|---|---|
| Isosorbide-5-mononitrate | — | 0.86 |
| Isosorbide-dinitrate | — | 17.5 |
| Propranolol | 331 | — |
| Pindolol | 104 | — |
| 1 | 2 326 | 0.77 |
| 2 (a) | — | 0.65 |
| 2 (b) | 4 164 | 0.68 |
| 2 (e) | 4 006 | 0.95 |
| 2 (g) | 4 158 | 0.97 |
| 6 | — | 2.75 |
| 4 (a) | 180 | 0.74 |
| 4 (c) | — | 1.95 |
| 6 (a) | 886 | 0.51 |
| 6 (c) | 2 273 | 1.34 |
| 7 | 1 619 | 1.72 |
| 8 | — | 0.48 |
| 9 (a) | 3 147 | 0.34 |
| 9 (c) | — | 1.63 |
| 9 (d) | — | 1.06 |
| 9 (f) | — | 1.23 |
| 9 (g) | — | 1.69 |
| 9 (h) | 1 207 | 1.06 |
| 9 (j) | — | 1.94 |

It will be understood that the specification and examples are illustrative but not limitative of the present invention and that other embodiments within the spirit and scope of the invention will suggest themselves to those skilled in the art.

What is claimed is:

1. A compound of the formula:

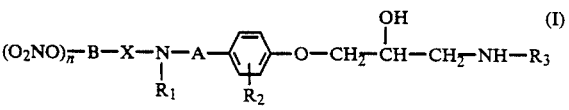

wherein A is a direct bond, an ethylene chain or a —CO—CH$_2$— group; X is a direct bond or a carbonyl group; B is a straight-chained or branched, saturated alkyl $C_1$-$C_6$ chain, in which one or two —CH$_2$— groups can also be replaced by a saturated $C_6$ cycloalkylene ring, n is 1, 2 or 3; $R_1$ is a hydrogen atom or a $C_1$-$C_4$ straight-chained or branched saturated alkyl or a —B—(ONO$_2$)$_n$ group, in which B and n have the same meanings as above, or when A is a —CO—CH$_2$— group and X is a direct bond, R$_1$ together with the nitrogen atom and a carbon atom of chain B can represent a piperidine ring; R$_2$ is a hydrogen, cyano, C$_1$-C$_4$ alkyl acetyl or ethoxycarbonyl; and R$_3$ is C$_3$-C$_5$ alkyl, 2-methyl-3-butyn-2-yl or 1-nitroxy-but-3-yl or a physiologically acceptable salt thereof.

2. A method for the treatment and prophylaxis of heart and circulatory diseases comprising administering 20-500 mg per day per 75 kg body weight of the compound of claim 1.

3. A pharmaceutical composition comprising an effective amount for the treatment and prophylaxis of heart and circulatory diseases of the compound of claim 1 in a pharmaceutically acceptable carrier.

4. The compound of claim 1 wherein the group

forms with a —CH$_2$— group of B a piperidine ring.

5. The compound of claim 1 wherein R$_2$ is selected from hydrogen, cyano, acetyl or ethoxycarbonyl.

6. The compound of claim 1 wherein the group

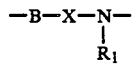

is a C$_2$-C$_4$-(alkylene)-carbonylamino, C$_5$-C$_6$-(cycloalkylene)-carbonylamino, cyclohexylenemethlcarbonylamino or ethyleneoxymethylcarbonylamino, piperidinyl or a methylenepiperidinyl group and A is a direct bond, an ethylene chain or a —CO—CH$_2$—group, n is 1, 2 or 3, R$_2$ is a hydrogen atom or a cyano, acetyl or ethoxycarbonyl group, R$_3$ is isopropyl, tert-butyl, 2-methyl-3-butyn-2-yl and 1-nitroxy-but-3-yl.

7. The compound of claim 1 designated 1-[4-[(2-nitroxypropyl)-amino]-carbonylmethyl]-phenoxy-3-tert.-butylaminopropan-2-ol hemifumarate.

8. The compound of claim 1 designated 1-[4-(3-nitroxypropyl)-carbonylamino]-phenoxy-3-tert.-butylaminopropan-2-ol hydrochloride.

9. The compound of claim 1 designated 1-[4-(4-nitroxymethyl-1-piperidino)-carbonylmethyl]-phenoxy-3-tert.-butylaminopropan-2-ol fumarate.

10. The compound of claim 1 designated 1-[2-methyl-carbonyl-4-(3-nitroxypropyl)-carbonylamino]-phenoxy-3-tert.-butylaminopropan-2-ol fumarate.

11. The compound of claim 1 designated 1-[2-cyano-4-(3-nitroxypropyl)-carbonylamino]-phenoxy-3-tert.-butylaminopropan-2-ol hydrochloride.

* * * * *

UNITED STATES PATENT AND TRADEMARK OFFICE
CERTIFICATE OF CORRECTION

PATENT NO. : 4,801,596            Page 1 of 2
DATED : January 31, 1989
INVENTOR(S) : Herbert Simon, et al.

It is certified that error appears in the above-identified patent and that said Letters Patent is hereby corrected as shown below:

Col. 11, line 29      after "(pale yellow oil"

insert -- ) --.

Col. 11, line 31
middle column      change "100 diethyl" to

-- 100 --.

right column      change "77-80 ether)" to

-- 77-80 (diethyl ether) --.

Col. 13, line 29      change "cyclohexyl]-r-1-carbonylamino-"

to -- .cyclohexyl]-r-1-carbonylamino]- --.

Col. 15, line 18      change "-phenoxy-3-" to

-- phenoxy- --.

Col. 16, line 18      change "trans-2,3-epoxy-1-[4-(2-nitroxycyclo-" to

-- trans-2,3-epoxy-1-[4-[(2-nitroxy-cyclo- --.

UNITED STATES PATENT AND TRADEMARK OFFICE
CERTIFICATE OF CORRECTION

PATENT NO. : 4,801,596

DATED : January 31, 1989

INVENTOR(S) : Herbert Simon, et al.

Page 2 of 2

It is certified that error appears in the above-identified patent and that said Letters Patent is hereby corrected as shown below:

Col. 17, line 2  change "4-[2-nitropropyl)-amino]-carbonyl-" to -- 4-[2-nitroxypropyl)-amino]-carbonyl- --.

Col. 17, line 12  change "N-methyl-N-(-nitroxypropyl)-" to -- N-methyl-N-(2-nitroxypropyl)- --.

Col. 17, line 47  change "unsufficiency" to -- insufficiency --.

Col. 19, line 7 in claim 1  after "alkyl" and before "acetyl" insert -- , --.

Signed and Sealed this

Fourteenth Day of November, 1989

Attest:

JEFFREY M. SAMUELS

Attesting Officer    Acting Commissioner of Patents and Trademarks